(12) United States Patent
Kubow et al.

(10) Patent No.: US 8,143,313 B2
(45) Date of Patent: Mar. 27, 2012

(54) COMPOSITIONS AND METHODS FOR PREVENTING OR TREATING AN INFLAMMATORY RESPONSE

(75) Inventors: Stan Kubow, Pointe Claire (CA); Regina Maria Vilela, Pointe Claire (CA); Larry Lands, Hampstead (CA)

(73) Assignee: McGill University, Montreal QC (CA)

( * ) Notice: Subject to any disclaimer, the term of this patent is extended or adjusted under 35 U.S.C. 154(b) by 0 days.

(21) Appl. No.: 12/829,612

(22) Filed: Jul. 2, 2010

(65) Prior Publication Data

US 2010/0267833 A1 Oct. 21, 2010

Related U.S. Application Data

(62) Division of application No. 10/591,481, filed as application No. PCT/CA2005/000323 on Mar. 2, 2005, now Pat. No. 7,754,769.

(60) Provisional application No. 60/548,908, filed on Mar. 2, 2004.

(51) Int. Cl.
  *A01N 37/18* (2006.01)
  *A01N 31/08* (2006.01)
  *A61K 31/16* (2006.01)
  *A61K 31/05* (2006.01)

(52) U.S. Cl. .................................. 514/613; 514/731
(58) Field of Classification Search .................. 514/613, 514/713
See application file for complete search history.

(56) References Cited

U.S. PATENT DOCUMENTS 4,665,098 A * 5/1987 Gibbs et al. .................. 514/613

FOREIGN PATENT DOCUMENTS

| CA | 2 365 290 | 9/2000 |
|----|-----------|--------|
| WO | WO 00/00207 | 1/2000 |
| WO | WO 01/02020 | 6/2000 |
| WO | WO 2004/064823 | 8/2004 |

OTHER PUBLICATIONS

Esposito et al."Effictiveness of infuenza vaccination of children with recurrent respiratory tract infections in reducing respiratory-related morbidity within the households" Vaccine, vol. 21, issue 23, Jul. 2003, pp. 3162-3168.*
Chan et al., "Ceramide Path in Human Lung Cell Death", Am. J. Respir. Cell Mol. Biol. 2000 22:460-468.
Erdreich-Epstein, "Ceramide Signaling in Fenretinide-induced Endothelial Cell Apoptosis", J. Biol. Chem. 2002 277 (51) :49531-49537.
Hannun et al., "Functions of Sphingolipids and Sphingolipid Breakdown Products in Cellular Regulation", Science 1989 243:500-507.
Lavrentiadou et al., "Ceramide-Mediated Apoptosis in Lung Epithelial Cells Is Regulated by Glutathione", Am. J. Respir. Cell Mol. Biol. 2001 25:676-684.
Liu et al., "Glutathione Regulation of Neutral Sphingomyelinase in Tumor Necrosis Factor-$\alpha$-induced Cell Death", J. Biol. Chem. 1998 273(18):11313-11320.
Luberto et al.,"Differential Effects of Sphingomyelin Hydrolysis and Resynthesis on the Activation of NF-κb in Normal and SV40-transformed Human Fibroblsts", J. Biol. Chem. 2000 275(19):14760-14766.
Maurer et al., "Increase of Ceramide and Induction of Mixed Apoptosis/Necrosis by N-(4-Hydroxyphenyl)-retinamide in Neuroblastoma Cell Lines", J. National Cancer Institute 19999 91(13):1138-1146.

* cited by examiner

*Primary Examiner* — Sreeni Padmanabhan
*Assistant Examiner* — Kendra D Carter
(74) *Attorney, Agent, or Firm* — Licata & Tyrrell P.C.

(57) ABSTRACT

The present invention relates to methods for modulating the inflammatory response of respiratory tract cells using an agent that increases ceramide levels in the cells of the respiratory tract.

1 Claim, 3 Drawing Sheets

COMPOSITIONS AND METHODS FOR PREVENTING OR TREATING AN INFLAMMATORY RESPONSE

INTRODUCTION

This application is a divisional of U.S. Ser. No. 10/591,481 filed Nov. 29, 2006, now U.S. Pat. No. 7,754,769 which is the U.S. National Phase of PCT/CA2005/000323 filed Mar. 2, 2005, which claims priority to U.S. Provisional No. 60/548,908 filed Mar. 2, 2004 each of which are herein incorporated by reference in their entireties.

BACKGROUND OF THE INVENTION

Cystic fibrosis is the most common lethal hereditary disease among Caucasians and it is characterized by a biochemical abnormality in CFTR (cystic fibrosis transmembrane conductance regulator) channel. The most common clinical manifestation in cystic fibrosis is chronic lung infection that leads to progressive tissue destruction and elevated pulmonary morbidity and mortality. Lung tissue damage in cystic fibrosis has been related to an abnormally exacerbated immune response in cystic fibrosis cells. This exacerbation has been related to an exaggerated activation of the pro-inflammatory transcriptional factor NF-κB.

One molecule that is known to inhibit NF-κB activation is ceramide (N-acylsphingosine; Signorelli, et al. (2001) *FASEB J.* 15:2401-2414), a sphingolipid recognized as a second messenger in the molecular modulation of apoptosis. The sphingomyelin cycle, with the conversion of sphingomyelin to ceramide by sphingomyelinase (SMase), is a key signaling pathway in many cell systems (Hannun, et al. (1996) *Science* 274(5294):1855-9). Two main routes have been defined for the generation of ceramide including hydrolysis of sphingomyelin, an abundant sphingolipid species in cell membranes, by the action of SMases; and by de novo biosynthesis catalyzed by ceramide synthase (Levade and Jaffrezou (1999) *Biochim. Biophys. Acta* 1438:1-17). The hydrolytic pathway, however, is the major source for ceramide in cellular responses to extracellular signaling, i.e., tumor necrosis factor-alpha (TNF-α), lipopolysaccharides, gamma-interferon, and interleukins (Chan and Goldkorn (2000) *Am. J. Respir. Cell Mol. Biol.* 22:460-468).

Treatment of cells in culture with TNF-α has emerged as one of the best-characterized models of cytokine-induction and of ceramide function. TNF-α induces activation of SMase in these cells and this activation is a consequence of the drop of glutathione that follows the activation of the death receptor and caspase 8 (Liu, et al. (1998) *J. Biol. Chem.* 273:11313-11320; Luberto, et al. (2000) *J. Biol. Chem.* 275:14760-14766). Conversely, extracellular supplementation of glutathione or N-acetylcysteine, a known precursor of glutathione, inhibit ceramide generation induced via oxidative stress caused by agents such as TNF-α, interleukin-1-β, hypoxia, and daunorubicin (Beaver and Waring (1995) *Eur. J. Cell Biol.* 68:47-54; Liu, et al. (1998) supra; Singh, et al. (1998) *J. Biol. Chem.* 273:20354-20362; Lavrentiadou, et al. (2001) *Am. J. Respir. Cell Mol. Biol.* 25:676-684). Glutathione inhibits the activation of the neutral, magnesium-dependent SMase and inhibits ceramide generation induced by TNF-α in human mammary carcinoma cells (Liu, et al. (1998) supra). In addition, it has been shown that low glutathione levels in lung cells were required for ceramide production, whereas high glutathione levels inhibit the generation of ceramide (Lavrentiadou, et al. (2001) supra).

Fenretinide, i.e., N-(4-hydroxyphenyl)retinamide (4-HPR) a synthetic derivative of retinoic acid, has been shown to increase endothelial ceramide by de novo, non-sphingomyelinase-mediated synthesis (Erdreich-Epstein, et al. (2002) *J. Biol. Chem.* 277:49531-49537) resulting in caspase-dependent endothelial apoptosis of human brain microvascular endothelial cells. Accordingly, fenretinide is suggested for use in cancer prevention.

U.S. Pat. No. 6,368,831 discloses a method of treating a hyperproliferative disorder (including tumors, cancers, and neoplastic tissue, along with pre-malignant and non-neoplastic or non-malignant hyperproliferative disorders) in a subject in need of such treatment using a ceramide-generating retinoid such as fenretinide and ceramide degradation inhibitor. This patent teaches that premalignant and non-neoplastic or non-malignant hyperproliferative disorders include but are not limited to myelodysplastic disorders; cervical carcinoma-in-situ; familial intestinal polyposes such as Gardner syndrome; oral leukoplakias; histiocytoses; keloids; hemangiomas; hyperproliferative arterial stenosis, inflammatory arthritis; hyperkeratoses and papulosquamous eruptions including arthritis.

U.S. Pat. No. 6,610,835 teaches that biologically important sphingolipids can be administered as prodrugs (e.g., ceramide β-glucuronide) which increase the level of active compound that is delivered to the active site of interest. The prodrug is cleaved by an appropriate enzyme in vivo to release a parent sphingolipid moiety for desired therapy. This reference teaches that the disclosed prodrugs are useful in the treatment of disorders of the lower intestinal tract, including but not limited to colon cancer, intestinal polyps, intestinal tumors, inflammatory bowel diseases including ulcerative colitis and Crohn's disease, necrotizing enterocolitis, ileocecitis, and other inflammations of the lower bowel.

SUMMARY OF THE INVENTION

The present invention is a method for inhibiting or reducing a pro-inflammatory response in a diseased cell of the respiratory tract. The method involves contacting the cell with an effective amount of an agent that increases ceramide levels in the cell thereby inhibiting or reducing a pro-inflammatory response in the cell.

The present invention is also a method for preventing acute respiratory inflammation in a subject. This method involves administering to a subject at risk of having acute respiratory inflammation an effective amount of an agent which increases ceramide levels in cells of the respiratory tract thereby preventing acute respiratory inflammation in the subject.

The present invention is further a method for inducing an inflammatory response in a cell. In accord with this method, a cell is contacted with an effective amount of an agent that increases the levels of ceramide in the cell thereby inducing an inflammatory response in the cell.

The present invention is also a method for decreasing proliferation of a diseased cell of the respiratory tract. The method involves contacting a diseased cell of the respiratory tract with an effective amount of an agent that increases the levels of ceramide in the cell thereby decreasing proliferation of the diseased cell of the respiratory tract Moreover, the present invention is a method for preventing a respiratory tract infection in a subject. The method involves administering to a subject at risk of acquiring a respiratory tract infection an effective amount of an agent which increases ceramide levels in cells of the respiratory tract thereby preventing a respiratory tract infection in the subject.

DETAILED DESCRIPTION OF THE INVENTION

Glutathione concentrations have been suggested to be relatively high in cystic fibrosis lung epithelial cells (Linsdell and Hanrahan (1998) *Am. J. Physiol.* 275:C323-326; Jungas, et al. (2002) *J. Biol. Chem.* 277:27912-8) and CFTR-deficient cells are less sensitive to oxidative stress induced by $H_2O_2$ than normal cells (Jungas, et al. (2002) supra), in part due to inherently high constitutive glutathione levels in the CFTR-deficient cells. To confirm the presence of high glutathione levels in CFTR-deficient cells, intracellular concentrations of total glutathione were determined in 9HTEo- human tracheal epithelial and CFTR ΔF508 tracheal epithelial (CFTE29o-) cell lines. The results of this analysis indicated that both the reduced form of glutathione (i.e., GSH) and the oxidized form of glutathione (i.e., GSSG) were 6.5- and 14-fold lower, respectively, in the non-cystic fibrosis epithelial cells (Table 1), indicating that non-cystic fibrosis cells lose intracellular GSH and GSSG due to CFTR-dependent transport.

TABLE 1

| Cell Line | GSSG (µM/mg protein) | GSH (µM/mg protein) |
| --- | --- | --- |
| 9HTEo– | *0.36 ± 0.09 | *2.5 ± 0.58 |
| CFTE29o– | 5.24 ± 0.44 | 16.23 ± 1.62 |

Data represents the mean concentrations ± S.E.M. from three separate experiments carried out on different days.
*Significantly different, p < 0.05.

Figure 1:
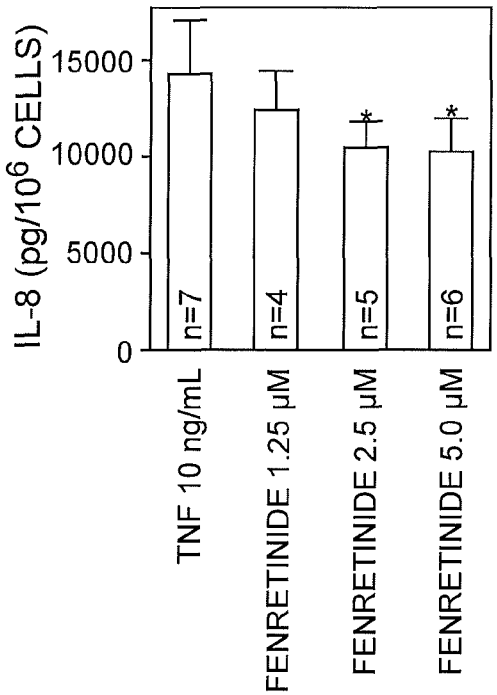
FIG. 1 shows the effect of fenretinide (1.25 µM, 2.5 µM and 5 µM) pretreatment on the release of IL-8 by CFTR-deficient cells (CFTE29o-) stimulated with human recombinant TNF-α. Results are means±S.E. of 4-7 independent experiments. *Significantly different (P<0.05) as compared to TNF-α control.
Figure 2:
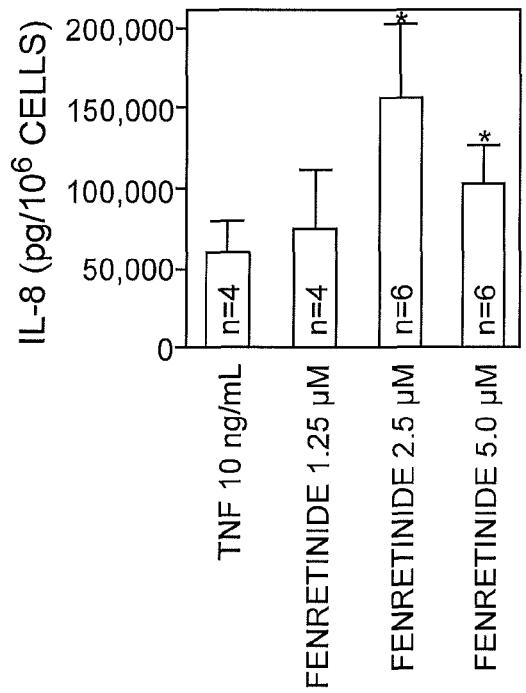
FIG. 2 shows the effect of fenretinide (1.25 µM, 2.5 µM and 5 µM) pretreatment on the release of IL-8 by normal cells (9HTEo-) stimulated with human recombinant TNF-α. Results are means±S.E. of 4-6 independent experiments. *Significantly different (P<0.05) as compared to TNF-α control.

Accordingly, taking into consideration that high concentrations of glutathione are present in CFTR-deficient cells, high glutathione levels have a negative effect on ceramide production (Liu, et al. (1998) supra), and ceramide can inhibit NF-κB activation that stimulates the release of pro-inflammatory cytokines such as IL-8 (Signorelli, et al. (2001) supra), it was determined whether supplementation of cystic fibrosis cells with an agent which enhances ceramide production could increase cellular ceramide concentrations to reduce NF-κB-dependent IL-8 release in response to a pro-inflammatory stimulus. Normal (9HTEo-) and CFTR-deficient (ΣCFTE29o- ΔF508 CFTR) human tracheal epithelial cells were treated with fenretinide (1.25, 2.5 or 5 µM) to induce ceramide production. Exposure of cells to 10 ng/mL TNF-α resulted in a 100-fold increase in secreted IL-8 levels in cystic fibrosis cells, whereas non-cystic fibrosis cells exhibited greater than 700-fold increase in IL-8 concentrations relative to the unstimulated controls (compare levels of IL-8 in FIGS. 1-2 to IL-8 levels in FIGS. 3-4, respectively). IL-8 was dose-dependently reduced by fenretinide in CFTR-deficient cells (FIG. 1) to 70% of the TNF-α-stimulated value, with a threshold level for significance at 2.5 µM. IL-8 levels were lowered to 86% of control in the cells exposed to the 1.25 µM fenretinide dose, but were not significantly different from the 100% control value containing only TNF-α. In contrast, IL-8 concentrations in normal lung epithelial cells in the pro-inflammatory state were enhanced by fenretinide (FIG. 2), to a maximum level of 139% of that secreted by TNF-α-stimulated cells, with an equally low threshold level of 2.5 µM. These results demonstrate that in CFTR-deficient lung epithelial cells, fenretinide can reduce the inflammatory immune hyper-responsiveness generated by the exaggerated activation of pro-inflammatory NF-κB.

Unstimulated non-cystic fibrosis and cystic fibrosis control cultures produced similar amounts of IL-8 with a trend for higher levels in association with cystic fibrosis cells. Sham treatment (ethanol) did not increase IL-8 secretion in either type of culture. Similarly, clinical studies have tended not to find any differences in cytokine levels between uninfected cystic fibrosis and control subjects (Armstrong, et al. (1995) Br. Med. J. 310:1571-1572). Also, P. aeruginosa infection has been demonstrated to occur intermittently in cystic fibrosis subjects as early as 3 years of age; hence, it has been suggested that detection of elevated IL-8 levels in cystic fibrosis subjects in some studies could be due to responses to a recently completed infection (Burns, et al. (2001). J. Infect. Dis. 183:444-4521).

Figure 3:
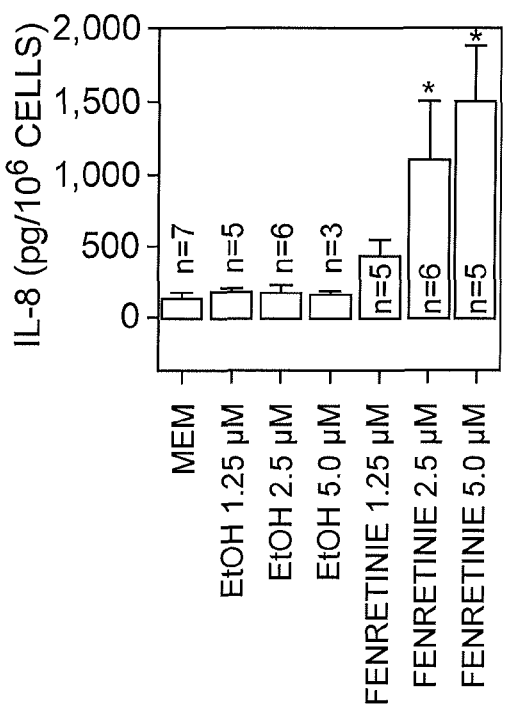
FIG. 3 shows the effect of fenretinide (1.25 µM, 2.5 µM and 5 µM) on the release of IL-8 by CFTR-deficient cells (CFTE29o-) under non-inflammatory conditions. Controls included minimum essential medium (MEM) and vehicle controls which contained ethanol (EtOH) at concentrations equivalent to those used with fenretinide treatments. Results are means±S.E. of 3-7 independent experiments. *Significantly different (P<0.05) as compared to MEM control.
Figure 4:
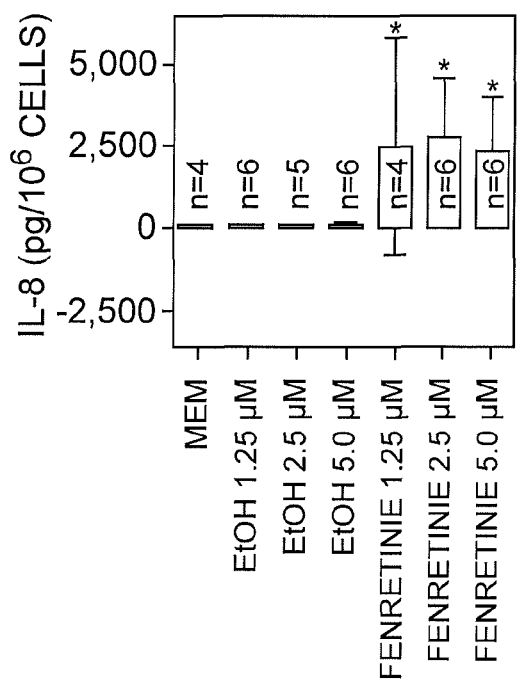
FIG. 4 shows the effect of fenretinide (1.25 µM, 2.5 µM and 5 µM) on the release of IL-8 by normal cells (9HTEo-) under non-inflammatory conditions. Controls included MEM and vehicle controls which contained EtOH at concentrations equivalent to those used with fenretinide treatments. Results are means±S.E. of 4-6 independent experiments. *Significantly different (P<0.05) as compared to MEM control.

In the absence of TNF-α stimulation, treatment with fenretinide increased the levels of IL-8 nearly 2- to 8-fold in cystic fibrosis cells in a dose-dependent manner (FIG. 3). Unexpectedly, cystic fibrosis cells were more resistant to the stimulatory effect of fenretinide on basal IL-8 release, as fenretinide treatment of non-cystic fibrosis cells at all treatment doses showed a greater enhancement in IL-8 release (greater than 14-fold; FIG. 4) than was observed with cystic fibrosis cells.

Figure 5:
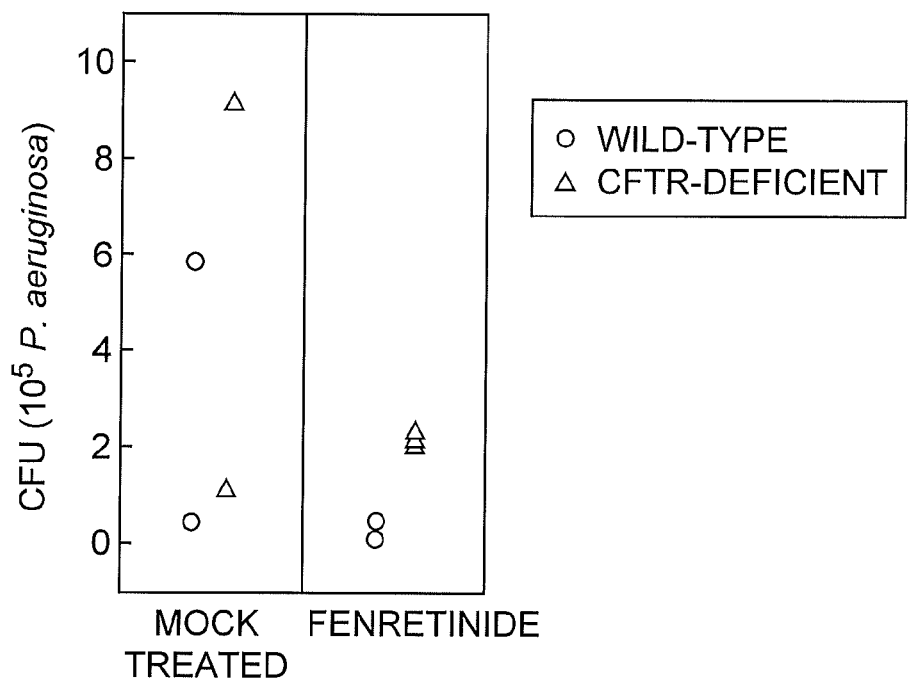
FIG. 5 shows the effect of fenretinide on the amount of *Pseudomonas aeruginosa* found in the lungs of wild-type and CFTR-deficient mice 3 days post-infection.
Figure 6:
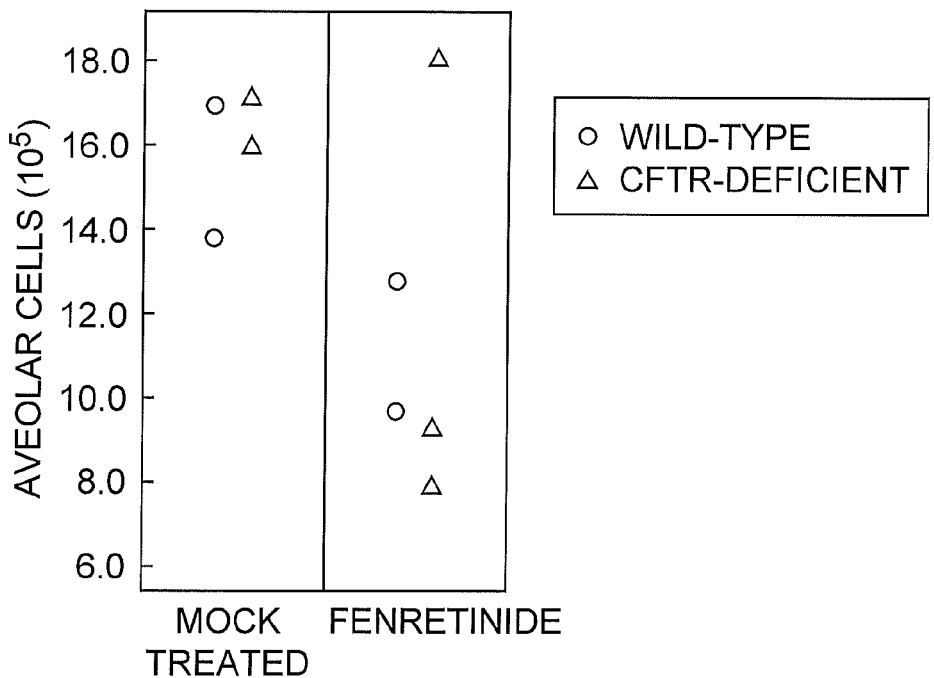
FIG. 6 shows the number of inflammatory cells recruited into the lungs of wild-type and CFTR-deficient mice pretreated with fenretinide and challenged with *P. aeruginosa*.

Subsequently, it was determined whether fenretinide could prevent or decrease infection of CFTR-deficient mice by Pseudomonas aeruginosa. Wild-type and CFTR-deficient mice were pretreated for one month with 5 mg/kg of fenretinide and subsequently challenged with P. aeruginosa. The bacterial burden in both the fenretinide-treated CFTR-deficient and wild-type mice was reduced at 3 days post-infection compared to one of the mock-treated control mice (FIG. 5). Fenretinide treatment also caused a decrease in the recruitment of inflammatory cells to the lungs of CFTR-deficient and wild-type mice at 3 days post-infection compared to mock-treated control mice (FIG. 6). These results indicate that fenretinide pretreatment can reduce infection by pathogenic organisms, decrease the acute inflammatory response in CFTR-deficient subjects, and further provide benefit to healthy subjects at risk of a respiratory tract infection.

A significant increase in cystic fibrosis intestinal epithelial cells regeneration has been observed due to an increased proliferation rate in CFTR-null mice and in cell culture (Gallagher and Gottlieb (2001) Am. J. Physiol. Gastrointest. Liver Physiol. 281:G681-G687). Further, cell proliferation has been shown to be greater in airway epithelia and nasal polyps in cystic fibrosis patients than in tissue from non-cystic fibrosis patients (Hassid, et al. (1997) J. Clin. Pathol. 50:923-928; Leigh, et al. (1995) Am. J. Respir. Cell Mol. Biol. 12:605-612) and to be attributable to differential expression of the CFTR (Gallagher and Gottlieb (2001) supra). The elevated cytosolic pH observed in cells expressing the CFTR mutation associated with cystic fibrosis can enhance the proliferation of these cells as cytosolic alkaline pH is a signal for mitogenesis (Elgavish (1991) Biochem. Biophys. Res. Commun. 180:342-348). Conversely, an overexpression of wild-type CFTR, but not mutant CFTR, results in the arrest of growth (Lesprit, et al. (2000) Histol. Histopathol. 15:395-402). Accordingly, it was determined whether the cells used in the instant analysis, exhibited increased rates of proliferation. The results of this analysis indicated that cystic fibrosis airway epithelial cells had an increased rate of proliferation relative to the wild-type cell line under both non-inflammatory (Table 2) and pro-inflammatory conditions (Table 3).

TABLE 2

| Cell Line | Cell numbers ($10^6$/mL) |
|---|---|
| 9HTEo– | *1.09 ± 0.83 |
| CFTE29o– | 1.64 ± 0.14 |

Cell proliferation in CFTR deficient (CFTE29o–) and normal (9HTEo–) human tracheal epithelial cells 72 hours after seeding. Data represents the mean concentrations ± S.E.M. from 4-7 separate experiments carried out on different days.
*Significantly different, $p < 0.05$.

TABLE 3

| Cell Line | Cell numbers ($10^6$/mL) |
|---|---|
| 9HTEo– | *0.82 ± 0.154 |
| CFTE29o– | 1.34 ± 0.74 |

Cell proliferation in CFTR deficient (CFTE29o–) and normal (9HTEo–) human tracheal epithelial cells 72 hours after seeding. Data represents the mean concentrations ± S.E.M. from 4-7 separate experiments carried out on different days.
*Significantly different, $p < 0.05$.

It has been suggested that increased proliferation of the airway CFTR-deficient epithelial cells, resulting from CFTR abnormalities, lung infection, injury or repair, could lead to a generally less mature and differentiated epithelium. In this regard, CFTR has been shown to play a key role in the differentiation of the respiratory epithelium during fetal lung development (Burns, et al. (2001) J. Infect. Dis. 183:444-452; Larson, et al. (2000) Am. J. Physiol. Lung Cell. Mol. Physiol. 279:L333-L341) and the development of the secretory epithelium (Larson, et al. (2000) supra). These events have, in turn, been implicated in decreased mucin biosynthesis and secretion. Chronic airway diseases, such as asthma, chronic bronchitis and cystic fibrosis are associated with mucus hypersecretion in airways leading to increased susceptibility to infection and decreased pulmonary function. Although patients with cystic fibrosis have increased airway secretions and poor mucus clearance, mucin content is diminished greatly in these secretions leading to increased susceptibility to airway infection in cystic fibrosis as P. aeruginosa binds to airway mucin (Ramphal and Arora (2001) Glycoconj. J. 18:709-713). Accordingly, mucin may act as a barrier to bacterial attachment to the epithelium and is likely important for the clearance of airway bacteria (Henke, et al. (2004) Am. J. Respir. Cell Mol. Biol. 31:86-91). Fenretinide has been demonstrated to suppress cell proliferation in several cancer cell lines (Ulukaya and Wood (1999) Cancer Treat. Rev. 25:229-35) and therefore, it was determined whether fenretinide had any effect on cell proliferation in cystic fibrosis cells. The results of this analysis indicate that in both the pro-inflammatory and non-inflammatory state, both CFTR-deficient and normal epithelial cells exhibit a significant decrease in cell proliferation, in particular at doses of 2.5 µM and higher (FIGS. 7-10).

Unexpectedly, the present results indicated that CFTR deficient epithelial cells, as opposed to non-cystic fibrosis epithelial cells, were resistant to the apoptotic effects of the cisplatin, which was used as a positive control for apoptosis. Cisplatin generates reactive oxygen species and triggers cellular responses involving multiple pathways, including DNA repair, transcription inhibition, cell cycle arrest, and apoptosis involving the c-Jun N-terminal kinase enzyme (JNK; stress-activated protein kinase) pathway (Siddik (2003)

*Oncogene* 22:7265-7279). Apoptosis has been suggested to be involved in the remodeling of lung tissue after acute lung injury for the clearance of excess epithelial stem cells after repair (Bardales, et al. (1997) *Am. J. Pathol.* 149:845-852) and for the normal removal of excess mesenchymal cells from resolving lesions (Polunovsky, et al. (1993) *J. Clin. Invest.* 92:388-397). There is also indication that rapid apoptosis of infected epithelial cells in cystic fibrosis may be critical for clearance of *P. aeruginosa* and CFTR-associated defects in apoptosis could be an important contributor to the pathogenesis of the lung disease in cystic fibrosis (Cannon, et al (2003) *Am. J. Respir. Cell Mol. Biol.* 29:188-97).

Figure 7:
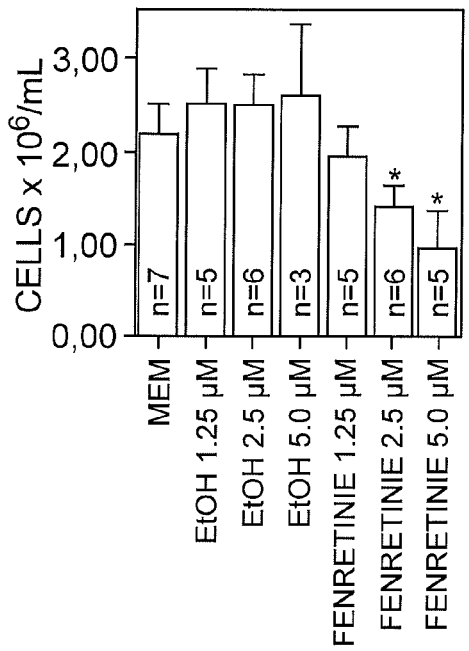
FIG. 7 shows the effect of fenretinide on proliferation of CFTR-deficient human epithelial cells (CFTE29o-). CFTE29o- ($0.6 \times 10^6$/well in a 24-well plate) cells were incubated with 1.25 µM, 2.5 µM or 5 µM of fenretinide for 24 hours in a MEM containing 10% FBS. Vehicle control wells contained ethanol (EtOH) at concentrations equivalent to those used with fenretinide treatments. After 24 hours, the medium was replaced by MEM 2% FBS, cells were incubated for another 24 hours and viable cell counts were determined. *Significantly different (P<0.05) as compared to MEM and carrier controls.
Figure 8:
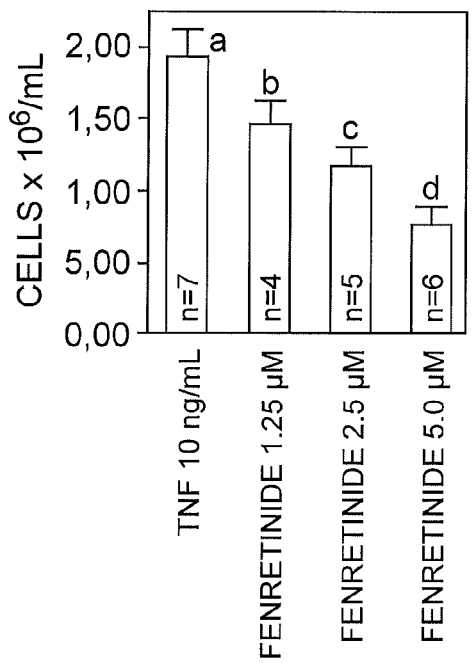
FIG. 8 shows the effect of fenretinide on proliferation of CFTR-deficient human epithelial cells stimulated with human recombinant TNF-α. CFTE29o- cells were incubated with 1.25 µM, 2.5 µM or 5 µM of fenretinide for 24 hours in a MEM containing 10% FBS. After 24 hours, the medium was replaced by MEM 2% FBS containing the same concentrations of fenretinide and stimulated with TNF-α for another 24 hours. Viable cell counts were determined. Means not sharing a common superscript are significantly different (P<0.05).
Figure 9:
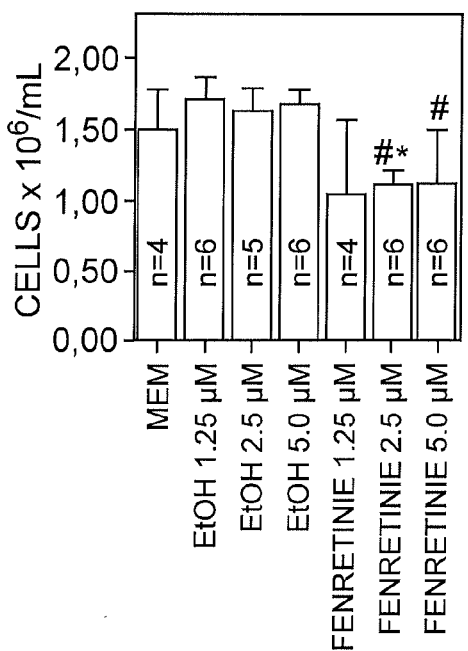
FIG. 9 shows the effect of fenretinide on proliferation of normal human epithelial cells (9HTEo-). 9HTEo- ($0.4 \times 10^6$/well in a 24-well plate) cells were incubated with 1.25 µM, 2.5 µM or 5 µM of fenretinide for 24 hours in a MEM containing 10% FBS. Vehicle control wells contained ethanol (EtOH) at concentrations equivalent to those used with fenretinide treatments. After 24 hours, the medium was replaced by MEM 2% FBS, cells were incubated for another 24 hours and viable cell counts were determined. *Significantly different (P<0.05) as compared to MEM. #Significantly different (P<0.05) as compared to carrier controls.
Figure 10:
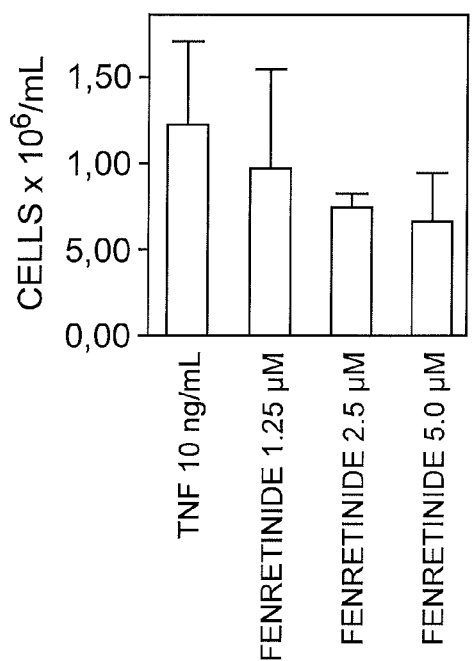
FIG. 10 shows the effect of fenretinide on proliferation of normal human epithelial cells stimulated with human recombinant TNF-α. 9HTEo- cells were incubated with 1.25 µM, 2.5 µM or 5 µM of fenretinide for 24 hours in a MEM containing 10% FBS. After 24 hours, the medium was replaced by MEM 2% FBS containing the same concentrations of fenretinide and stimulated with TNF-α for another 24 hours. Viable cell counts were determined. *Significantly different (P<0.05) as compared to TNF-α control.

Accordingly, it was determined whether fenretinide had any influence on apoptosis under pro-inflammatory conditions. It was found that fenretinide treatment, at an effective dose of 2.5 µM, was associated with a decrease in CFTR-deficient epithelial cell numbers in the non-inflammatory condition. Since the fenretinide dose of 2.5 µM was associated with early stage apoptosis, as assessed by fluorescein staining, a diminution in cell proliferation rather than cell death was responsible for the lower cell numbers (FIG. 7). This indicates that the anti-proliferative effect of fenretinide was mediated via changes in intracellular ceramide as ceramide and sphingosine, along with their phosphorylated derivatives, play an important role as second messengers involved in regulating cell proliferation, differentiation and apoptosis (Hannun and Bell (1989) *Science* 243:500-507). Unexpectedly, the lower fenretinide dose of 1.25 µM, which was not associated with a statistically significant decrease in IL-8 secretion in cystic fibrosis cells, also did not show a decrease in cell numbers. Although the cells showed no morphology of apoptosis, weak fluorescence was observed, signifying that the cells may have been in the very early stages of apoptosis. In contrast to cystic fibrosis cells, the lower cell numbers observed in non-cystic fibrosis epithelial cells at the fenretinide dose of 2.5 µM appeared to be due to apoptotic cell death as strong fluorescence and classic apoptotic morphology was observed. The lower fenretinide dose of 1.25 µM showed weaker fluorescence and an earlier stage of apoptosis. In the presence of TNF-α, however, no enhancement of apoptosis was observed in CFTR-deficient epithelial cells at either of the fenretinide doses. On the other hand, significant apoptosis was observed with both doses of fenretinide treatment of non-cystic fibrosis cells treated with TNF-α.

Having demonstrated that low dose fenretinide can act to attenuate inflammation in the pro-inflammatory state, the present invention is a method for inhibiting or reducing a pro-inflammatory response in a diseased cell of the respiratory tract using an agent that increases ceramide levels in the cell. This method of the present invention involves the steps of contacting a cell with an effective amount of an agent that increases ceramide levels in the cell thereby inhibiting or reducing a pro-inflammatory response in the cell. In particular embodiments of the present invention, the cell has been or is at risk of being exposed to a pro-inflammatory stimulus which produces the pro-inflammatory response. A pro-inflammatory response can arise as a result of an infection by a bacterium, virus, or fungus; however, an infection is not required to initiate a pro-inflammatory response. For example, smoking (Noguera, et al. (2001) *Thorax.* 56(6):432-7), TNF-α, allergen exposure, exposure to an endotoxin in the absence of bacterial infection, and bacterial flagellin (Llaudet, et al. (2003) *Shock* 19:131-137) are considered pro-inflammatory stimuli which facilitate a pro-inflammatory response in the context of the instant invention.

This method of the present invention is particularly suitable for inhibiting or reducing a pro-inflammatory response in a diseased cell of the respiratory tract (i.e., nasal and oral passages, nasopharynx, oropharynx, trachea or lung cell) which is hyper-responsive to pro-inflammatory stimuli. A diseased cell of the respiratory tract is generally considered a cell which has a pre-existing condition which can arise from a number of causes, including inhalation of toxic agents, accidents, harmful lifestyles such as smoking, infections, genetic factors, and anything else that affects development, either directly or indirectly, thereby predisposing the cells of the respiratory tract to respond to pro-inflammatory stimuli in a hyper-responsive manner. Diseased cells of particular interest are cells having a respiratory tract disease including, but are not limited to, asthma, inflammatory airway disease, bronchitis, emphysema, pneumonia, chronic obstructive pulmonary disease (COPD), respiratory distress syndrome, influenza, epiglottitis, tuberculosis, and cystic fibrosis. In particular embodiments, the respiratory tract cell is a lung cell. In other embodiments, the respiratory tract disease is cystic fibrosis.

The pro-inflammatory response in the diseased cell is inhibited or reduced by contacting the cell with an agent that increases ceramide levels in the cell. Suitable agents that can be used in accord with the methods of the present invention include agents which increase the de novo synthesis of ceramide, decrease the hydrolysis of ceramide, increase the hydrolysis of ceramide-conjugates, or decrease the use of ceramide as a substrate, or combinations thereof.

Agents which increase the de novo synthesis of ceramide are well-known in the art and include, but are not limited to, palmitic acid, serine, THC analogues, gemcitabine, vitamin C, vaspodar, camptothecin, etoposide, paclitaxel, fludarabine, all-trans-retinoic acid (ATRA) and retinoic acid derivatives (see, e.g., Radin (2003) *Biochem. J.* 371:243-256). U.S. Pat. No. 6,774,114 also teaches a monosaccharide ester of ascorbic acid and/or at least one metal salt of phosphorylated ascorbic acid for increasing the synthesis of ceramide. In particular embodiments, the agent selected is ATRA or a retinoic acid derivative such as all-trans-N-(4-hydroxyphenyl)retinamide or C-glycoside analogs of N-(4-hydroxyphenyl)retinamide-O-glucuronide. Such compounds and their preparation are known and described in U.S. Pat. Nos. 5,663, 377 and 5,599,953. Specific examples of such compounds include 4-(retinamido)phenyl-C-glucuronide; 4-(retinamido)phenyl-C-glucoside; 4-(retinamido)phenyl-C-xyloside; 4-(retinamido)benzyl-C-glucuronide; 4-(retinamido)benzyl-C-glucoside; 4-(retinamido)benzyl-C-xyloside; 1-(.beta.-D-glucopyranosyl) retinamide; and 1-(D-glucopyranosyluronosyl) retinamide. In particular embodiments, the agent used increase ceramide levels in the cell is all-trans-N-(4-hydroxyphenyl)retinamide, i.e., fenretinide, which has CAS registry number 65646-68-6. Fenretinide is particular suitable for use in the present methods as it is reported to have fewer side-effects compared to naturally-occurring retinoids including vitamin A (Ulukaya and Wood (1999) *Cancer Treat Rev.* 25:229-35). The safety profile for fenretinide is excellent as minimal side-effects have been noted in a variety of clinical trials using fenretinide on a prophylactic basis (Ulukaya and Wood (1999) supra). Clinical trials have shown that fenretinide does not induce generalized vascular damage in humans (Reynolds and Lemons (2001) *Hematol. Oncol. Clin. North Am.* 15:867-910). Fenretinide has also been used to treat subjects (2-21 years of age) with neuroblastoma to define fenretinide pharmacokinetics and maximal tolerated dose in children, and to assess short- and mid-term toxicity in this age range (Garaventa, et al. (2003) *Clin. Cancer Res.* 9:2032-2039). Fenretinide was given orally once a day in 28-day courses. Liver and renal functions and clinical evaluation were assessed weekly. The side effects that occurred in 15 of the 45 subjects tested were the same as those observed in adult subjects. The side effects were noted to be tolerable and readily reversible within 7 days following discontinuation of the treatment.

Agents which decrease the hydrolysis of ceramide include inhibitors of ceramidase which converts ceramide to sphingosine and fatty acid. Particularly suitable inhibitors of ceramidase include N-oleyolethanolamine, D-MAPP, and derivatives thereof, e.g., p-nitro-D-MAPP (see, e.g., Radin (2003) supra).

Agents which decrease the use of ceramide as a substrate include, but are not limited to, glucosylceramide synthase inhibitors, 1-acylceramide synthase inhibitors (also referred to as 1-O-acylceramide synthase inhibitors), and sphingosine-1-phosphate synthesis inhibitors. Glucosylceramide synthase inhibitors and/or 1-acylceramide synthase inhibitors are known and are disclosed, for example, in U.S. Pat. No. 5,302,609; U.S. Pat. No. 5,041,441 and U.S. Pat. No. 5,707,649. Specific examples of glucosylceramide synthase inhibitors include, but are not limited to, 1-phenyl-2-acylamino-3-morpholino-1-propanol; 1-phenyl-2-decanoylamino-3-morpholino-1-propanol (PDMP); D-threo-1-phenyl-2-palmitoylamino-3-pyrrolidino-1-propanol (PPPP); 1-phenyl-2-palmitoylamino-3-morpholino-1-propanol (PPMP); ethylenedioxy-P4; mifepristone; N-butyl deoxynojirimycin; anti-androgens; and Tamoxifen, including tamoxifen citrate. Sphingosine-1-phosphate synthesis inhibitors including sphingosine kinase inhibitors such as D-erythro-N,N-dimethylsphingosine are known. For example, sphingosine kinase inhibitor F12509A is disclosed in Japanese Patent Application 9176083.

Agents which increase the hydrolysis of ceramide-conjugates, such as glucosylceramide, are also intended for use in accord with the methods of the present invention. Such agents include, but are not limited to, acidic phospholipids such as bis(monoacylglycero)-phosphate and PtdSer, vitamin A, saposin C analogs, and chlorpromazine (CPZ) (see, e.g., Radin (2003) supra).

Additional active compounds for increasing ceramide levels in the cell can be generated by known techniques, including rational drug design techniques and/or random drug design techniques (or combinatorial chemistry techniques) targeting particular enzymes which hydrolyze or synthesize ceramide or use existing active compounds as lead compounds. Methods for determining the three-dimensional structure of active compounds and producing active analogs thereof are known, and are referred to as rational drug design techniques. See, e.g., U.S. Pat. Nos. 5,593,853; 5,612,895; 5,331,573; 4,833,092; 4,859,765; 4,853,871; and 4,863,857. In combinatorial chemistry (or random drug design) techniques, large combinatorial libraries of candidate compounds are screened for active compounds therein. Libraries used to carry out the present invention can be produced by any of a variety of split synthesis methods. Split synthesis methods in which a releasable tag is attached to the particle along with the organic compounds of interest are also known as cosynthesis methods. A variety of such methods are known. See, e.g., Furka, et al. (1991) *J. Pept. Protein Res.* 37:487; Lam, et al. (1991) *Nature* 354:82; Zuckermann, et al. (1992) *Int. J. Pept. Protein Res.* 40:498; Sebestyen, et al. (1993) *Bioorg. Med. Chem. Lett.* 3:413; and Lam, et al. (1993) *Bioorg. Med. Chem. Lett.* 3:419.

An effective amount of the agents disclosed herein is an amount which inhibits or reduces the pro-inflammatory response mediated by increased cellular ceramide levels; an effect which can be determined by monitoring the expression or secretion of pro-inflammatory cytokines such as IL-8, IL-6, granulocyte-macrophage colony stimulating factor (GM-CSF), and the like. Desirably, the agent decreases the expression or secretion of a pro-inflammatory cytokine in the cell by about 10%, 20%, 30%, 40%, 50%, 60%, 70%, 80%, 90% or 100% as compared to the same cell in the absence of the agent. In one embodiment, the agent decreases the expression of at least one pro-inflammatory cytokine by at least 10% as compared to the same cell in the absence of the agent. In another embodiment, the agent decreases the expression of at least one pro-inflammatory cytokine by at least 30% as compared to the same cell in the absence of the agent.

By inhibiting or reducing a pro-inflammatory response in a diseased cell, this method of the present invention will be useful for studying the signaling pathways involved in the pro-inflammatory response and for preventing acute respiratory inflammation in a subject at risk.

Normally, acute inflammation occurs for a short period of time. If an infection is not cleared during this period of time, the inflammation shifts from being acute to chronic and involves lymphocytes and macrophages. The shift to chronic inflammation is generally desirable because chronic inflammation is less damaging to tissue. In patients with cystic fibrosis, however, the acute inflammatory response fails to make the transition to a chronic response. Advantageously, the data presented herein indicates that pre-treatment with a ceramide up-regulating drug such as fenretinide can ameliorate acute lung inflammation in respiratory tract diseases such as cystic fibrosis. Accordingly, the present invention is also a method for preventing or reducing acute respiratory inflammation by administering to a subject at risk of having acute respiratory inflammation an effective amount of an agent which increases ceramide levels in cells of the respiratory tract.

As used herein, an acute inflammatory response is generally characterized as inflammation dominated by neutrophils, as well as eosinophil recruitment. In the acute inflammatory state, IL-8 and leukotriene B4 production is increased, neutrophils infiltrate the lung where they release mediators, such as elastase, that further inhibit host defenses, cripple opsonophagocytosis, impair mucociliary clearance, and damage airway wall architecture (Chmiel and Davis (2003) *Respir Res.* 4(1):8). The combination of these events favors the persistence of microorganisms in the airway. Accordingly, attenuating the acute inflammatory response will limit damage to host tissues and speed recovery.

Subjects who can particularly benefit from receiving an agent which increases ceramide levels in cells are those suffering from a pre-existing respiratory tract disease (e.g., those disclosed herein) and are at risk of being exposed to a pro-inflammatory stimulus which results in an acute inflammatory response. Such exposure can include being in the vicinity of an individual known to have a respiratory tract infection such as *Haemophilus influenzae, P. aeruginosa, Streptococcus, Tuberculosis, Candida albicans* or *Aspergillus fumigatus*, for example. To prevent or reduce an acute inflammatory response, the subject at risk is administered an effective amount of an agent disclosed herein, desirably in a pharmaceutically acceptable formulation, to prevent or reduce the acute inflammatory response. An amount effective to produce prevention or reduction, is an amount as discussed supra, or in the context of therapy is an amount which decreases or attenuates the signs or symptoms of acute inflammation or abbreviates the acute inflammatory response in the subject being treated when compared to a subject who has not received preventive treatment. Signs or symptoms of acute inflammation which can be monitored to assess effectiveness of treatment include, but are not limited to swelling, redness, fever, pain, wheezing, mucociliary clearance, and the like.

A subject, as used in the context of the present invention, is intended to include humans; companion animals such as dogs, cats, and birds; livestock such as cows, pigs, and chickens; and any other mammal (e.g., horses) which may receive benefit from the therapeutic methods of the instant invention.

Agents which increase ceramide levels in the cell can be prepared for therapeutic use in accordance with the methods disclosed herein by formulating the agents with a pharmaceutically acceptable carrier. In the manufacture of a pharmaceutical formulation, the active agent including the physiologically acceptable salt thereof, is typically admixed with, inter alia, an acceptable carrier. The carrier must, of course, be acceptable in the sense of being compatible with any other ingredients in the formulation and must not be deleterious to the subject. The carrier can be a solid or a liquid, or both, and is preferably formulated with the compound as a unit-dose formulation, for example, a tablet, which can contain from 0.5% to 95% by weight of the active agent. One or more active agents can be incorporated in the formulations of the invention, which can be prepared by any of the well-known techniques of pharmacy consisting essentially of admixing the components, optionally including one or more accessory ingredients. See, e.g., Remington: The Science and Practice of Pharmacy, Alfonso R. Gennaro, editor, 20th ed. Lippingcott Williams & Wilkins: Philadelphia, Pa., 2000

The formulations of the invention include those suitable for oral, buccal (e.g., sub-lingual), parenteral (e.g., subcutaneous intramuscular, intradermal, or intravenous), and topical (i.e., mucosal surfaces and airway surfaces) administration, although the most suitable route in any given case will depend on the nature and severity of the condition being treated and on the nature of the particular active agent which is being used. Of particular interest are formulations for oral, buccal or topical administration. It is contemplated that the formulations of the instant invention can be used alone or in combination with other therapeutics currently used to treat respiratory tract diseases disclosed herein.

Formulations suitable for oral administration can be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations can be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet can be prepared by compressing or molding a powder or granule containing the active agent, optionally with one or more accessory ingredients. Compressed tablets can be prepared by compressing, in a suitable machine, the compound in a free-flowing form, such as a powder or granules optionally mixed with a binder, lubricant, inert diluent, and/or surface active/dispersing agent (s). Molded tablets can be made by molding, in a suitable machine, the powdered compound moistened with an inert liquid binder.

Formulations suitable for buccal (sub-lingual) administration include lozenges having the active agent in a flavored base, usually sucrose and acacia or tragacanth; and pastilles containing the active agent in an inert base such as gelatin and glycerin or sucrose and acacia.

Formulations for parenteral administration are conveniently sterile aqueous preparations of the active agent, which preparations are preferably isotonic with the blood of the intended recipient. These preparations can be administered by means of subcutaneous, intravenous, intramuscular, or intradermal injection. Such preparations can conveniently be prepared by admixing the compound with water or a glycine buffer and rendering the resulting solution sterile and isotonic with the blood.

Formulations suitable for topical application (e.g., in the oral passage, nasopharynx, or oropharynx) take the form of an ointment, cream, lotion, paste, gel, spray, aerosol, or oil. Carriers which can be used include vaseline, lanoline, polyethylene glycols, alcohols, transdermal enhancers, and combinations of two or more thereof.

Formulations suitable administration to the trachea or lungs can be in the form of liquid or solid formulations. Formulations are desirably administered as particles of respirable size, e.g., particles of a size sufficiently small to pass through the nose, mouth and larynx upon inhalation and through the bronchi and alveoli of the lungs. In general, respirable particles range from about 0.5 to 10 microns in size. Particles of non-respirable size which are included in the aerosol tend to deposit in the throat and be swallowed, and the quantity of non-respirable particles in the aerosol is thus minimized. For nasal administration, a particle size in the range of 10-500 microns is desirable to ensure retention in the nasal cavity.

Solid particulate compositions containing respirable dry particles of micronized active agent can be prepared by grinding dry compound with a mortar and pestle, and then passing the micronized composition through a 400 mesh screen to break up or separate out large agglomerates. A solid particulate composition containing the active agent can optionally contain a dispersant which serves to facilitate the formation of an aerosol. A suitable dispersant is lactose, which can be blended with the active agent in any suitable ratio, e.g., a 1 to 1 ratio by weight.

Aerosols of solid particles containing the active agent and surfactant can be produced with any solid particulate medicament aerosol generator. Aerosol generators for administering solid particulate medicaments to a subject produce particles which are respirable, and generate a volume of aerosol containing a predetermined metered dose of a medicament at a rate suitable for human administration. One illustrative type of solid particulate aerosol generator is an insufflator. Suitable formulations for administration by insufflation include finely comminuted powders which can be delivered by means of an insufflator or taken into the nasal cavity in the manner of a snuff. In the insufflator, the powder, e.g., a metered dose thereof effective to carry out the treatments described herein, is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend containing the active ingredient, a suitable powder diluent, such as lactose, and an optional surfactant. The active ingredient is typically from 0.1 to 100 weight/weight (w/w) of the formulation. A second type of illustrative aerosol generator is a metered dose inhaler. Metered dose inhalers are pressurized aerosol dispensers, typically containing a suspension or solution formulation of the active ingredient in a liquified propellant. During use, these devices discharge the formulation through a valve adapted to deliver a metered volume, typically from 10 to 150 µL, to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation can additionally contain one or more co-solvents, for example, ethanol, emulsifiers and other formulation surfactants, such as oleic acid or sorbitan trioleate, anti-oxidants and suitable flavoring agents.

Aerosols of liquid particles containing an active agent of the present invention can be produced by any suitable means, such as with a nebulizer. See, e.g., U.S. Pat. No. 4,501,729. Nebulizers are commercially available devices which transform solutions or suspensions of the active ingredient into a therapeutic aerosol mist either by means of acceleration of a compressed gas, typically air or oxygen, through a narrow venturi orifice or by means of ultrasonic agitation. Suitable formulations for use in nebulizers contain the active ingredient in a liquid carrier in an amount of up to 40% w/w preferably less than 20% w/w of the formulation. The carrier is typically water or a dilute aqueous alcoholic solution, preferably made isotonic with body fluids by the addition of, for example, sodium chloride. Optional additives include preservatives if the formulation is not prepared sterile, for example, methyl hydroxybenzoate, anti-oxidants, flavorings, volatile oils, buffering agents and emulsifiers and other formulation surfactants.

An aerosol, whether formed from solid or liquid particles, can be produced by an aerosol generator at a rate of from about 10 to 150 liters per minute, more generally from about 30 to 150 liters per minute, and most desirably about 60 liters per minute. Aerosols containing greater amounts of medicament can be administered more rapidly.

An effective amount or dose of any one active agent will vary somewhat from compound to compound, subject to subject, and will depend upon factors such as the condition of the subject and the route of delivery. Such dosages can be determined in accordance with routine pharmacological procedures known to those skilled in the art, particularly in light of the disclosure provided herein and current dosing practices of known active agents.

For example, fenretinide has been used systemically by achieving a plasma level of about 0.1, 2, 3, 5 μM to 10 or 20 μM. Typically (for oral dosing) 50 or 100 to 500 or 1000, 2000 or 3000 mg/m$^2$ body surface area per day is used. In particular embodiments, 0.1 to 10 μM plasma concentrations are achieved.

For tamoxifen, a serum level of 1.5 to 2 μM achieves a clinically desirable effect, and these levels can be achieved at a dosage of about 150 to 300 or 500 mg/day of tamoxifen citrate p.o., or at 300 or 400 to 500 or 700 mg/m$^2$ per day. These levels are achievable on a pulse-dose basis using higher p.o. dosing of 400-500 mg/day.

Inhibition of basal IL-8 release results in reduced influx of neutrophils and lymphocytes to the site of tissue damage with an increased susceptibility to respiratory infections (Greenberger, et al. (1996) *J. Infect. Dis.* 173:159). Neutrophils may also aid in restoration of epithelial integrity after injury and cytokines such as IL-8, IL-6, and IL-10 can enhance wound closure in epithelial cells (Zahm, et al. (2000) J. Cell Physiol. 185:447-453). Further, neutrophil depletion in rats has resulted in decreased epithelial proliferation and repair following ozone-induced epithelial injury (Vesely, et al. (1999) *Am. J. Respir. Cell Mol. Biol.* 20:699-709). The results provided herein indicate that in the absence of a pro-inflammatory stimulus, an agent which increases ceramide levels in the cell can increase basal IL-8 levels in both normal and diseased cells. Accordingly, the present invention is a method for inducing an inflammatory response in a cell by contacting the cell with an effective amount of an agent that increases the levels of ceramide in the cell.

In particular embodiments, the inflammatory response is a pro-inflammatory or acute inflammatory response mediated by pro-inflammatory cytokine production (e.g., IL-8, IL-6 and the like) which chemoattract neutrophils. It is contemplated that the cell to be treated is a normal, healthy cell or a diseased cell (e.g., those disclosed herein) of the respiratory tract. The amount of agent used to achieve the desired effect of inducing an inflammatory response may vary with the cell type used and can be determined by measuring pro-inflammatory cytokine production. For example, as exemplified herein, basal IL-8 levels could be increased by contacting normal cells with very low levels of fenretinide (e.g., 1.25 μM; FIG. 4), whereas CFTR-deficient cells required higher levels of fenretinide (e.g., 5 μM; FIG. 3) to achieve similar levels of IL-8 release. In general, an effective amount, in the context of this method of the present invention, is an amount which induces or enhances an inflammatory response; an effect which can be determined by monitoring the expression or secretion of pro-inflammatory cytokines such as IL-8, IL-6, granulocyte-macrophage colony stimulating factor (GM-CSF), and the like. Desirably, the agent causes at least a 2-fold increase in pro-inflammatory cytokine expression or secretion. More desirably, the agent causes a 5-fold, 10-fold, 15-fold, 20-fold or higher increase in the expression or secretion of a pro-inflammatory cytokine in the cell as compared to the same cell in the absence of the agent.

By inducing an inflammatory response in a cell, this method of the present invention will be useful for studying the signaling pathways involved in the inflammatory response and for protecting subjects at risk against respiratory infections.

Fenretinide has also been shown to overcome the anti-apoptotic action and enhanced proliferation seen in cystic fibrosis cells. Accordingly, the present invention further provides a method for reducing or decreasing proliferation of a diseased cell of the respiratory tract with an effective amount of an agent that increases, the levels of ceramide in the cell. An effective amount of an agent that increases the levels of ceramide in the cell is an amount which decreases the proliferation of the disease respiratory tract cell as compared to a cell not contacted with the agent. Rates of cell proliferation can be determined in accordance with standard methods well-known to the skilled artisan. Because ceramide-inducing agents such as fenretinide by-pass the blockage of apoptotic mechanisms in diseased cells such as cystic fibrosis cells, this method of the present invention is useful for studying the pathophysiology of respiratory tract diseases as well as facilitating the maturation and differentiation of epithelial cells of the respiratory tract thereby protecting individuals with respiratory tract diseases from acquiring respiratory tract infections.

Having demonstrated that cystic fibrosis mice pretreated with fenretinide and challenged with *P. aeruginosa* exhibited an approximately 40% reduction in *P. aeruginosa* cell numbers as compared to controls (FIG. 5), the present invention is also a method for preventing or reducing a respiratory tract infection in a subject by administering to a subject at risk of acquiring a respiratory tract infection an effective amount of an agent which increases ceramide levels in cells of the respiratory tract. Subjects who can particularly benefit from this method of the present invention include healthy subjects and, in particular embodiments, subjects having a pre-existing respiratory tract disease, wherein the subject is at risk of having been exposed to a respiratory tract infection such that increased pro-inflammatory cytokine levels and neutrophil recruitment can decrease susceptibility to the respiratory tract infection. In the context of the present teachings, it is contemplated that the enhanced basal release of IL-8 and decreased rate at which epithelial cells proliferate and differentiate, could lead to a generally more mature and differentiated epithelium thereby enhancing mucin biosynthesis and secretion to improve the capability of cystic fibrosis patients to combat recurrent lung infections and improve the restorative capacity of the lung tissue post-infection.

Respiratory tract infections which can be prevented or reduced (as determined by cell or viral counts) include, but are not limited to, common cold viruses (e.g., rhinoviruses, coronaviruses, adenoviruses, myxoviruses, echoviruses, Coxsackie A and B); dental caries causes by *Streptococcus mutans*; thrush caused by *C. albicans*; trench mouth caused by *Treponema vincentii* or *Fusobacterium fusiforme*, stomatitis caused by herpes simplex virus; pharyngitis caused by adenovirus, herpes simplex virus, coxsackieviruses, *S. pyrogenes*, or *Corynebacterium diphtheriae*; croup caused by parainfluenza viruses or respiratory syncytial virus; epiglottitis caused by *H. influenzae*; bronchitis caused by parainfluenza viruses, respiratory syncytial virus, influenza viruses, *M. pneumoniae, C. pneumoniae*; bronchiolitis caused by respiratory syncytial virus; or other infections known to the cause respiratory tract disease (e.g., *P. aeruginosa, Mycobacterium tuberculosis*, or *Aspergillus fumigatus*). In particular embodiments, the respiratory track infection prevented or reduced is an infection of the lungs.

To prevent or reduce a respiratory tract infection, the subject at risk is administered an effective amount of an agent disclosed herein, desirably in a pharmaceutically acceptable formulation, to prevent or reduce the respiratory tract infection. An amount effective to produce prevention or reduction is an amount which causes a specified increase in pro-inflammatory cytokine expression or secretion (e.g., as discussed supra), or in the context of therapy efficacy is an amount which decreases or attenuates the signs or symptoms of respiratory tract infection or abbreviates the respiratory tract infection in the subject being treated when compared to a subject who has not received preventive treatment. Suitable effective amounts are disclosed herein and can vary with the infection and the patient being treated. Signs or symptoms of respiratory tract infection which can be monitored to assess effectiveness of treatment include, but are not limited to cell or viral counts, fever, mucociliary clearance, and the like. Such signs or symptoms can be evaluated by the skilled clinician before and after treatment with the active agent to evaluate the effectiveness of the treatment regime and dosages can be adjusted accordingly.

The invention is described in greater detail by the following non-limiting examples.

Example 1

Materials

Normal (9HTEo-) and CFTR-deficient ΣCFTE29o- (ΔF508 homozygote) human tracheal epithelial cells are art-established cell cultures for analyzing the pathophysiology of cystic fibrosis and the inflammatory response in these respiratory epithelial cells (Gruenert, et al. (1988) *Proc. Natl. Acad. Sci. USA* 85:5951-5955; Clemens, et al. (2000) *Infect. Immun.* 68(8):4430-40; Cromwell, et al. (1992) *Immunology* 77(3):330-7; Schwiebert, et al. (1999) *Am. J. Physiol.* 276(3 Pt 1):C700-10; Scheid, et al. (2001) *Eur. Respir. J.* 17:27-35). Studies using epithelial cell cultures from cystic fibrosis patients (Δ508-CFTR) have correlated well with the pathophysiology of cystic fibrosis. For example, Rubenstein, et al. ((1997) *J. Clin. Invest.* 100:2457-2465) teach that 4-phenylbutyrate (4PBA) treatment at concentrations of 0.1-2 mM resulted in restoration of forskolin-activated chloride secretion in Δ508-CFTR cell cultures. Likewise, a 19 gram dose t.i.d. given to 18 Δ508-CFTR homozygous patients with cystic fibrosis was sufficient to statistically improve the nasal potential difference response pattern in these patients to perfusion of an isoproterenol/amiloride/chloride-free solution, a measure that reflects epithelial CFTR function.

Cell culture supplies such as minimum essential medium, fetal bovine serum (FBS), penicillin-streptomycin, L-glutamine, and Dulbecco's phosphate-buffered saline (PBS) were obtained from GIBCO-BRL™ (Grand Island, N.Y.). Trypsin-EDTA solution (0.25%) was obtained from Sigma-Aldrich Co (St. Louis, Mo.). The solution used to coat the T-75 flasks and 24-well plates was prepared with collagen type I bovine, and human fibronectin obtained from BD Biosciences (San Jose, Calif.). EGTA, BSA, and LHC basal medium was obtained from Biofluids Biosource (Camarillo, Calif.). Human recombinant TNF-α was obtained from BD PHARMINGEN™ (San Diego, Calif.) and prepared with 0.1% BSA. To determine IL-8 release, ELISA kits (OPTEIA™ Human IL-8 Set) were obtained from BD Bioscience (San Diego, Calif.). Cell viability was determining using MTT obtained from Sigma-Aldrich Co. (St. Louis, Mo.). N-(4-hydroxyphenyl)-retinamide (i.e., fenretinide) was obtained from Sigma-Aldrich Co (St. Louis, Mo.).

Example 2

Cell Cultures

General Procedures. Normal (9HTEo-) and CFTR-deficient human tracheal epithelial cells (CFTE29o- ΔF508 CFTR) were used in the analysis disclosed herein and grown in pre-coated T-75 flasks in a medium containing 10% fetal bovine serum (FBS). Cells were re-fed every 2-3 days until they reached confluency. Adherent monolayers were released from the plastic surface after treatment with trypsin-EDTA (Sigma-Aldrich Co., St. Louis, Mo.) and split into 24-well plates for about 24 hours before receiving treatments.

Treatment with Fenretinide and TNF-α. Normal and CFTR-deficient cells were treated with fenretinide (Wang, et al. (2001) *Cancer Res.* 61:5102-5105; Erdreich-Epstein, et al. (2002) supra) at doses known to effectively increase cellular ceramide content in cell culture. Normal (9HTEo-; $0.4 \times 10^6$ cells/well) and CFTR-deficient human epithelial cells (CFTE29o- ΔF508 CFTR; $0.6 \times 10^6$ cells/well) were incubated for 24 hours at 37° C. in 5% $CO_2$ with 1.25 µM, 2.5 µM or 5 µM fenretinide in Eagle's minimum essential medium (MEM) containing 10% fetal bovine serum (FBS). Subsequently, the medium was replaced with fresh MEM 2% FBS containing the same initial concentrations of fenretinide and cells were grown for an additional 24 hours to characterize the impact of fenretinide on IL-8 release in a non-inflammatory condition. To characterize the inflammatory condition, cells were treated with MEM 2% FBS containing 1.25 µM, 2.5 µM or 5 µM fenretinide and concurrently stimulated with human recombinant TNF-α (10 ng/mL) for another 24 hours. All experiments included unstimulated negative control wells.

IL-8 Release and Cell Viability Assays. Supernatants were collected from treated cells and the amount of IL-8 released into the medium was determined using an enzyme-linked immunosorbent assay (ELISA) kit (OPTEIA™ Human IL-8 Set; BD PHARMINGEN™, San Diego, Calif.). Briefly, 96-well plates were coated overnight with capture antibody, washed with PBS, 0.05% TWEEN®-20 and coated with PBS, 10% heat-inactivated FBS. Known concentrations of IL-8 (standard) and supernatants containing released IL-8 were added as aliquots into appropriate wells, incubated for 2 hours and subsequently decanted from the wells. Enzyme-conjugated anti-IL-8 antibody was added and incubated for 1 hour. After washing the plate, a substrate for the enzyme was added and the plate incubated for 30 minutes. The reaction was stopped using a $2NH_2SO_4$ solution and the absorbance was read at 450 nm.

Cell viability was assessed using a 3-(4,5-dimethylthiazol-2-yl)-2,5-diphenyltetrazolium bromide (MTT) assay according to standard methods (Mosmann, T. (1983) *J. Immunol. Methods*. 65:55-63). Briefly, after collecting supernatant to determine IL-8 release, cells were gently washed with PBS and MTT solution (0.5 mg/mL MTT in culture medium free of phenol red) was added. Cells were incubated for 4 hours at 37° C., supernatant was aspirated, HCl-isopropanol solution (0.04 N HCl in isopropanol) was added, and after 5 minutes the optical densities were measured at 540 nm. The test is based upon formation of a blue formazan product produced by the reduction of the yellow MTT tetrazolium salt by mitochondrial reductases. Color intensity correlates with cell number and metabolic activity of the cells. In cells with equal activity, the test can be used to determine the percentage of viable cells.

Example 3

Intracellular Glutathione Measurements

Quantitative determination of the total intracellular GSH and glutathione disulfide (GSSG) was performed according to standard methods (Yang, et al. (2002) *Biomed. Chromat.* 16:224-228) with the following modifications. Confluent normal and CFTR-deficient tracheal epithelial cells in six-well plates were washed twice with 5.0 mL PBS containing 25 mg % BSA. The cells were treated with 1.5 mL volume of 25 mg % BSA in PBS solution and then subjected to centrifugation at 500×g for 10 minutes followed by another centrifugation at 400×g for 6 minutes. The supernatant was discarded and the cells were washed once with 0.45 mL PBS and re-suspended with 0.45 mL PBS. Samples were diluted with 0.1 mL 10 mM HCl and sonicated for 3 cycles of 20 seconds. The cell suspension was filtered using a centrifugal MILLIPORE™ filter (#42407; MILLIPORE™, Billerica, Mass.) at 14,000×g for 60 minutes at 4° C. The protein concentration of the unfiltered portion of the samples was determined by the Bradford assay (BIO-RAD®, Waltham, Mass.). The filtrates were transferred to a 96-well microplate for measurement of GSH and GSSG concentrations using a GSH reductase recycling method (Anderson (1985) *Meth. Enzymol*. 113:548-551) following treatment of the samples with 5,5'-dithiobis-2-nitrobenzoic acid (DTNB). The microplate was placed on the microtiter plate reader using a 420-nm filter and absorbance was read for 5 minutes. Samples were compared with the calibration curve to determine the GSH and GSSG concentrations in each well.

Example 4

In Situ End Labeling of DNA Strand Breaks

Adherent epithelial cell lines, CFTE29o- and 9HTEo-, grown on coated coverslips for 24 hours, were treated with fenretinide at the same concentrations used to determine IL-8 release as indicated supra. After a 24-hour incubation with fenretinide, cells were stimulated with TNF-α (experimental group) or with Cisplatin at 25 mg/mL or 12.5 mg/mL (as a positive control) for an additional 24 hours. Cells were fixed in 4% paraformaldehyde in PBS at pH 7.4 for one hour at room temperature. Cells were subsequently washed and permeabilized using 0.1% TRITON™ X-100 in 0.1% citrate buffer for 2 minutes on ice. After being washed, the coverslips were individually removed from 24-well plates and cells were incubated for one hour at 37° C. with terminal deoxynucleotidyl transferase (Tdt) enzyme conjugated to fluorescein (Roche Diagnostics, Indianapolis, Ind.) for visualization. A negative slide was produced by incubating a slide of both cell lines with buffer minus the Tdt enzyme. The Tdt enzyme binds to the free hydroxyl end of DNA strand breaks. Subsequently, cells were washed twice with PBS and coverslips were placed on slides in the presence of the anti-fade medium VECTASHIELD® to facilitate fluorescence preservation. Slides were individually labeled with numbers to keep the investigator blinded to the outcome until after the slides were reviewed. Four randomly selected fields were visualized at 400× (total magnification) using a fluorescence microscopy and cells that appeared brightly flourescent were counted. Pictures were taken to estimate the number of positive to negative cells per field.

Example 5

Statistical Analysis

The minimum number of replicates for all measurements was at least three. All cytokine data are expressed as mean±SEM for all studies performed. Comparisons between values of the cytokines were made using analysis of variance (ANOVA). Student's t-tests were performed on the GSH and GSSG data. Data were considered to be significant when $P<0.05$.

Example 6

Infection of CFTR Knockout Mice with *P. aeruginosa*

Homogenous C57BL/6 Cftr$^{unc}$ knockout mice generated by insertion of a stop codon in exon 10 of Cftr gene are well-known in the art (Snouwaert, et al. (1992) *Science* 257: 1083-8; Gosselin, et al. (1998) *Am. J. Respir. Crit. Care Med.* 157:1253-62). Mice used in these studies represent offsprings from B6-Cftr$^{unc}$ (+/−) mice backcrossed to C57BL/6 mice for 10 to 12 generations.

Housing Conditions. B6-Cftr (−/−) and B6-Cftr (+/+) mice were housed on corn cob bedding (Anderson, Maumee, Ohio) and fed sterile PEPTAMEN® (Clintec Nutrition, Deerfield, Ill.), a low-residue liquid diet which was previously shown to prevent intestinal obstruction in Cftr$^{unc}$ knockout mice (Eckman, et al. (1995) *Am. J. Physiol.* 269:L625-L630). A standard diet was used (Gosselin, et al. (1998) supra), wherein the caloric content of the diet was 420 KJ/100 mL and an adult mouse consumes approximately 15 mL/day. In order to maintain the sterility of the diet, it was changed daily. For one month prior to pulmonary infection with *P. aeruginosa*, mice were provided fenretinide (prepared in PEPTAMEN®) in the drinking water at 5 mg/kg body weight. The dose was set for each individual mouse based on its weight and adjusted every week (e.g., 147 μg/mouse/day for 30 gram mouse).

Infection of Mice. *P. aeruginosa* (strain 508) initially isolated from a cystic fibrosis patient was selected for mucoid character. Pulmonary infection with this strain of bacteria, entrapped in agar beads, is established in the art (Gosselin, et al. (1995) *Infect. Immun.* 63:3272-3278; Morissette, et al. (1995) *Infect. Immun.* 63:1718-1724; Stevenson, et al. (1995) *Clin. Exp. Immunol.* 99:98-105). Briefly, a log-phase suspension of bacteria was diluted in warm (52° C.) trypticase soy agar (TSA). The bacteria was then entrapped in agar beads by mixing with heavy mineral oil (52° C.) (Fischer Scientific, Fair Lawn, N.J.) and stirring vigorously followed by cooling of the mixture at 4° C. The bacteria-containing beads were washed extensively and resuspended in PBS (ICN Biomedicals Inc., Costa Mesa, Calif.). The size ($\leq$150 μM) and uniformity of the beads were confirmed by microscopic examination. The number of viable *P. aeruginosa* entrapped in agar beads was determined by plating serial dilutions of the homogenized bead suspension on TSA plates.

Mice were anesthetized with a mixture of ketamine hydrochloride (75 mg/kg body weight; MTC Pharmaceuticals, Cambridge, Ontario, Canada) and xylazine (30 mg/kg body weight; Bayvet Division, Chemagro Limited, Etobicoke, Ontario, Canada) injected intramuscularly. A 50-μL inoculum, containing $10^5$ viable *P. aeruginosa* entrapped in agar beads, was injected into the lungs through the trachea with a 22-gauge intravenous catheter (Critikon, Tampa, Fla.).

Bronchoalveolar Lavages (BAL). The alveoli of infected mice were washed 7 times with one mL of PBS via the cannulated trachea. Alveolar cells were centrifuged, resuspended in 1 mL PBS, stained with Turk's solution and counted. The proportions of macrophages, lymphocytes, and polymorphonuclear leukocytes (PMN) were calculated after counting 200 alveolar cells on cytospin preparations stained with DIFF-QUICK® (American Scientific Products, McGaw Park, Ill.).

Measurement of Bacterial Burden. Lungs, spleen, kidneys, and livers were harvested independently from infected mice and homogenized for 60 seconds at high speed (homogenizer PT10135; Brinkmann Instruments Co., Mississauga, Ontario, Canada) in 10 mL of PBS. Serial 10-fold dilutions of homogenates were plated on petri dishes containing TSA and the number of colony-forming units (CFU) per organs was counted after overnight incubation at 37° C. In each experiment, the identity of the bacteria recovered from infected animals was confirmed using a VITEK® gram-negative identification system (BioMérieux Vitek, Inc., Hazelwood, Mo.).

What is claimed is:

1. A method for reducing acute respiratory inflammation in a subject with cystic fibrosis comprising administering an effective amount of fenretinide to a subject with cystic fibrosis, wherein said subject is at risk of acquiring a respiratory tract infection, wherein said respiratory tract infection is selected from the group consisting of *Haemophilus influenza, Pseudomonas aeruginosa, Streptococcus, Tuberculosis, Candida albicans,* and *Aspergillus fumigatus,* so that the acute respiratory inflammation is reduced.

* * * * *